United States Patent
Mayo

(12)
(10) Patent No.: US 6,302,689 B1
(45) Date of Patent: Oct. 16, 2001

(54) DISPOSABLE IMPRESSION TRAYS FOR EDENTULOUS DENTAL RIDGES

(76) Inventor: Louis J. Mayo, 1340 Hill Crest Rd., Cincinnati, OH (US) 45224-3226

(*) Notice: Subject to any disclaimer, the term of this patent is extended or adjusted under 35 U.S.C. 154(b) by 0 days.

(21) Appl. No.: 09/818,815

(22) Filed: Mar. 27, 2001

(51) Int. Cl.[7] .................................... A61C 9/00
(52) U.S. Cl. .............................................. 433/37
(58) Field of Search .................. 433/37, 41, 42, 433/43, 44, 45, 46, 47, 48; 128/859

(56) References Cited

U.S. PATENT DOCUMENTS

| | | | |
|---|---|---|---|
| 55,465 | 6/1866 | Buttles | 433/37 |
| 90,802 | 6/1869 | Wuestenberg | 433/37 |
| 1,509,376 | 9/1924 | Rodgers | 433/37 |
| 3,473,225 | * 10/1969 | Deuschle et al. | 433/48 |
| 3,619,903 | 11/1971 | Schreinemakers | 433/37 |
| 4,173,219 | 11/1979 | Lentine | 128/260 |
| 4,227,877 | 10/1980 | Tureaud et al. | 433/37 |
| 4,530,662 | 7/1985 | Andersson et al. | 433/37 |
| 4,569,342 | 2/1986 | von Nostitz | 128/136 |
| 4,657,509 | 4/1987 | Morris | 433/37 |
| 4,768,951 | 9/1988 | Abiru et al. | 433/48 |
| 5,076,785 | 12/1991 | Tsai | 433/46 |
| 5,135,392 | 8/1992 | Polansky | 433/37 |
| 5,336,086 | 8/1994 | Simmen et al. | 433/37 |
| 5,427,117 | 6/1995 | Thornton | 128/848 |
| 5,554,024 | 9/1996 | Ueda | 433/37 |
| 6,017,217 | 1/2000 | Wittrock | 433/37 |
| 6,237,601 | * 5/2001 | Kittelsen et al. | 128/859 |

FOREIGN PATENT DOCUMENTS 2619704 3/1989 (FR).

OTHER PUBLICATIONS

"Impression Materials", Condensation Silicone, http://www.coltenewhaledent.com/imptray.htm, 1 page.
"Nickel Plated", GCA—Impression Trays, http://www.g-camerica.com/coemet.asp, 2 pages.
"COE Brand", GCA—Impression Trays, http://www.g-camerica.com/ptry.asp, 4 pages.

* cited by examiner

Primary Examiner—John J. Wilson
(74) Attorney, Agent, or Firm—Steven J. Rosen

(57) ABSTRACT

A disposable dental impression tray for making impressions of edentulous dental arches with impressionable material is made of plastic or some other inexpensive material and includes a thin contoured plate having a contour approximating a section of an oral cavity of a mouth of which an impression is to be made. The plate has a impression side for holding impressionable material and an opposite backside. A reinforced edge runs around at least a portion or border of the plate and cross-bracing extends along the backside. A handle located at a front of the plate extends generally normal to and away from the backside of the plate and has a flat surface on a front and/or a back of the handle. Holes extend through the plate between the impression side and the backside and are located along the plate between cross-ribs of the bracing. The holes are flared outwardly from the impression side to the backside.

23 Claims, 5 Drawing Sheets

DISPOSABLE IMPRESSION TRAYS FOR EDENTULOUS DENTAL RIDGES

BACKGROUND OF THE INVENTION

1. Field of the Invention

This invention relates to anatomically shaped disposable dental impression trays formed of thermoplastic material and having reinforced edges and cross-bracing.

2. Discussion of the Background Art

To form an accurate impression of a dentulous or edentulous alveolar ridge, in the course of producing a male model of desired oral tissues, conventional practice involves the use of commercially available initial impression trays for use with either the maxillary or the mandibular alveolar ridges and contiguous tissues, in either dentulous or edentulous cases. These trays are available in a range of sizes so that one which makes an approximate fit with the patient's mouth shape and size may be chosen for use. They have a cross-section characterized by a channel with two normally extending walls so that they will surround the ridge of which an impression is to be formed. The contours of these trays are not anatomical in the sense that they are adapted to abut or lie in close proximity to the gum area surrounding the ridge, but rather a tray is chosen which fits within the patient's mouth and loosely surrounds the tooth or gum section. The tray is constructed to fit over the general structures of the dental anatomy and constructed in many lengths, widths and with varying degrees of curvature, and is used to transport and hold in place a substance, often referred to as impression material and which, when hardened, creates an accurate negative image of the structures in the mouth.

These stock trays are typically formed of aluminum, stainless or plated steel, hard plastic, or other material that may be bent or trimmed at the edges to improve the fit to an individual patient. Impression material is placed in the tray and a female cast of the required area is formed. This cast is then typically used to form an initial male model of the patient's mouth section either in the dental office or in a separate dental laboratory. The dental office or laboratory then uses this male model to form a custom final impression tray out of a plastic material. This tray is anatomical in that it closely adapts to the male model and is relieved in the muscle attachments and other contiguous tissue areas.

The dentist then uses this custom tray to form a final impression of the required area by placing a high definition, settable, impression material such as polyvinylsiloxane, polyether or the like, into the impression tray. This conventional practice typically requires two separate procedures with two patient appointments and is relatively expensive and time consuming.

A number of alternative means for forming final impressions have been proposed to overcome these recognized inadequacies of the conventional procedure. For example, several forms of stock trays have been devised which may be shaped exteriorly of the mouth to improve the accuracy of initial impressions.

When a patient is edentulous (i.e. has no teeth in the dental arch), a dental tray designed with a high degree of curvature to take an impression of the teeth and immediate surrounding tissue is not adequate for this function. Using such a tray results in impressions of the dental ridge is inaccurate and not suitable for full denture construction. Disposable dental impression trays presently available have shorter heights or lesser arches, more suitable to the contours of the edentulous dental ridges but distort easily under the load of impression material when transported and placed in the mouth under sufficient pressure to seat or mold the impression. When such a tray is removed from the mouth and the seating pressure is relieved, the tray springs back to its unstressed form and bends or distorts the impression. The flexibility of the tray is worsened as the size of the back end flanges increase and the dental ridge flattens.

This is more evident with disposable dental impression trays for impression taking of the mandible where the tray's horse-shoe or U-shaped, allowing for a space to accommodate the tongue, markedly reduces the rigidity of the dental tray. The distortion of the impression has the consequence of ultimately causing a newly made denture to be poorly fitting.

There is, thus, a need to develop an inexpensive disposable dental tray for the edentulous ridge that is both thin and sufficiently rigid to minimize distortion of the tray during impression taking of edentulous dental ridges and subsequent distortion of the impression resulting therefrom.

SUMMARY OF THE INVENTION

A disposable dental impression tray for making impressions of edentulous dental arches with impressionable material is made of plastic or some other inexpensive material and includes a thin contoured plate having a contour approximating a section of an oral cavity of a mouth of which an impression is to be made. The plate has an impression side for holding impressionable material and an opposite backside. A reinforced edge runs around at least a portion of a border of the plate and cross-bracing extends along the backside.

An exemplary embodiment of the invention includes a handle located at a front of the plate and extending generally normal to and away from the backside. The handle has a flat surface on a front and/or a back of the handle. The maxillary tray has the flat surface on the back of the handle and the mandibular tray has the flat surface on the front of the handle. The maxillary tray has another flat surface on the front of the handle. Holes extend through the plate between the impression side and the backside and are located along the plate between cross-ribs of the bracing. The holes are flared outwardly from the impression side to the backside. The plate has a U-shaped trough and the trough has a U-shaped cross-section. The U-shaped trough has legs extending back and away from the front of the plate. In one particular embodiment, the tray is a maxillary tray and the contour approximates maxillary gums and a roof of a mouth. The maxillary tray has a flat surface on a back of the handle. In another particular embodiment, the tray is a mandibular tray and the plate is a generally U-shaped trough with rear arched flanges extending down from a rear of the tray and the contour approximates mandibular gums of a mouth. Elongated inner and outer lingual bracing members are disposed on the backside of the plate and spaced apart from the edges of the mandibular tray. The mandibular tray has a flat surface on the front of the handle.

BRIEF DESCRIPTION OF THE DRAWINGS

The novel features believed characteristic of the present invention are set forth and differentiated in the claims. The invention is more particularly described in conjunction with the accompanying drawings in which:

DETAILED DESCRIPTION

While there have been described herein what are considered to be preferred and exemplary embodiments of the present invention, other modifications of the invention shall be apparent to those skilled in the art from the teachings herein and, it is therefore, desired to be secured in the appended claims all such modifications as fall within the true spirit and scope of the invention.

Figure 1:
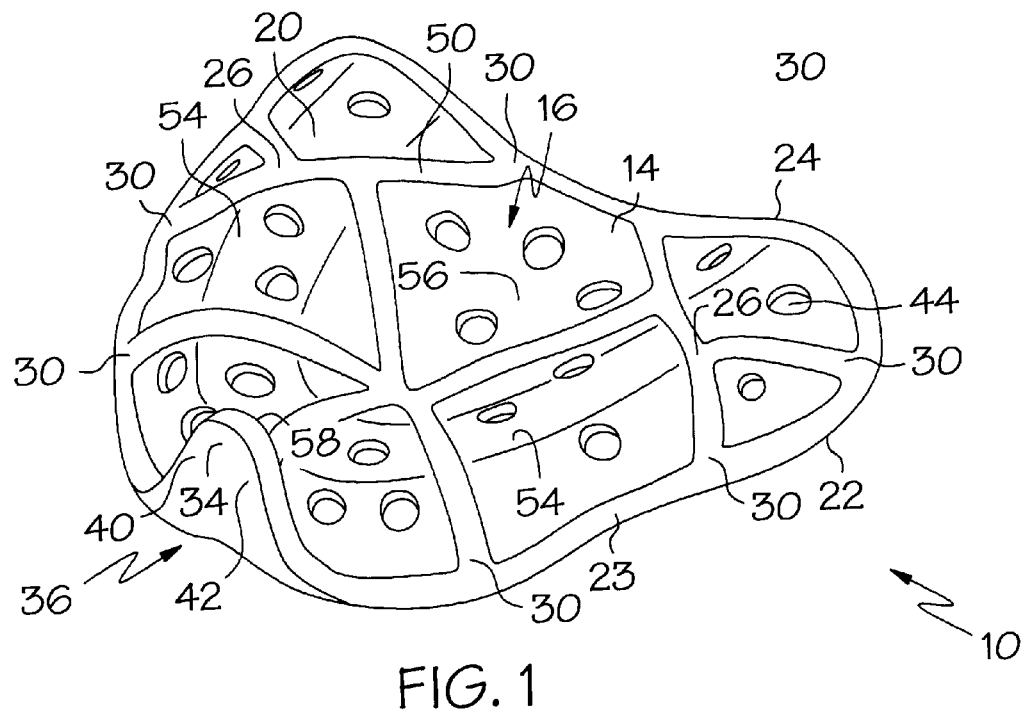
FIG. 1 is a forward looking aft top perspective view illustration of an exemplary embodiment of a maxillary impression tray of the present invention.
Figure 2:
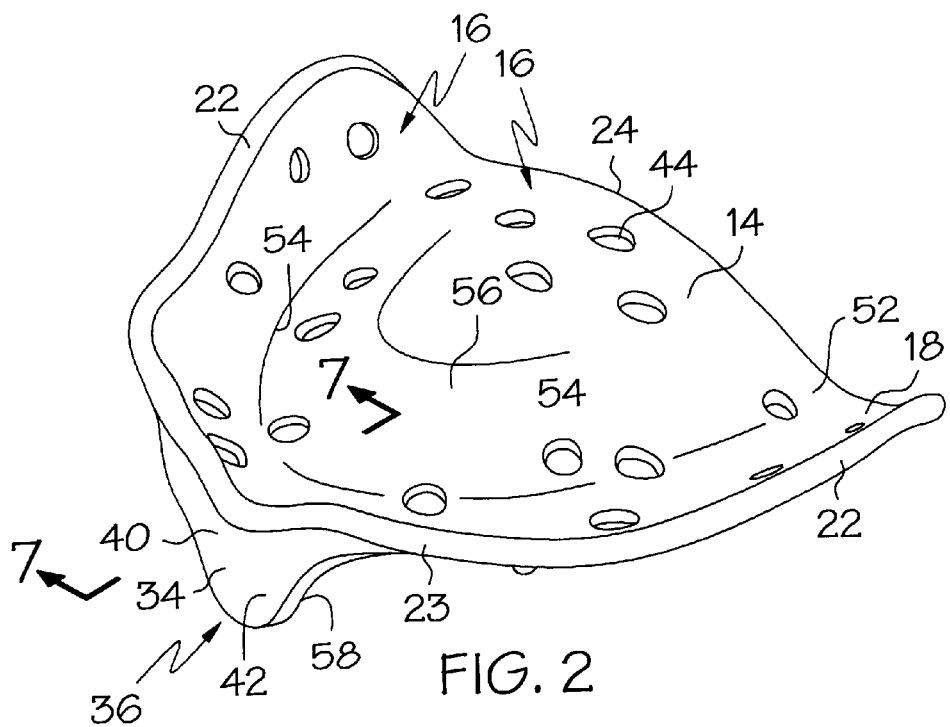
FIG. 2 is a forward looking aft bottom perspective view illustration of the maxillary impression tray illustrated in FIG. 1.
Figure 3:
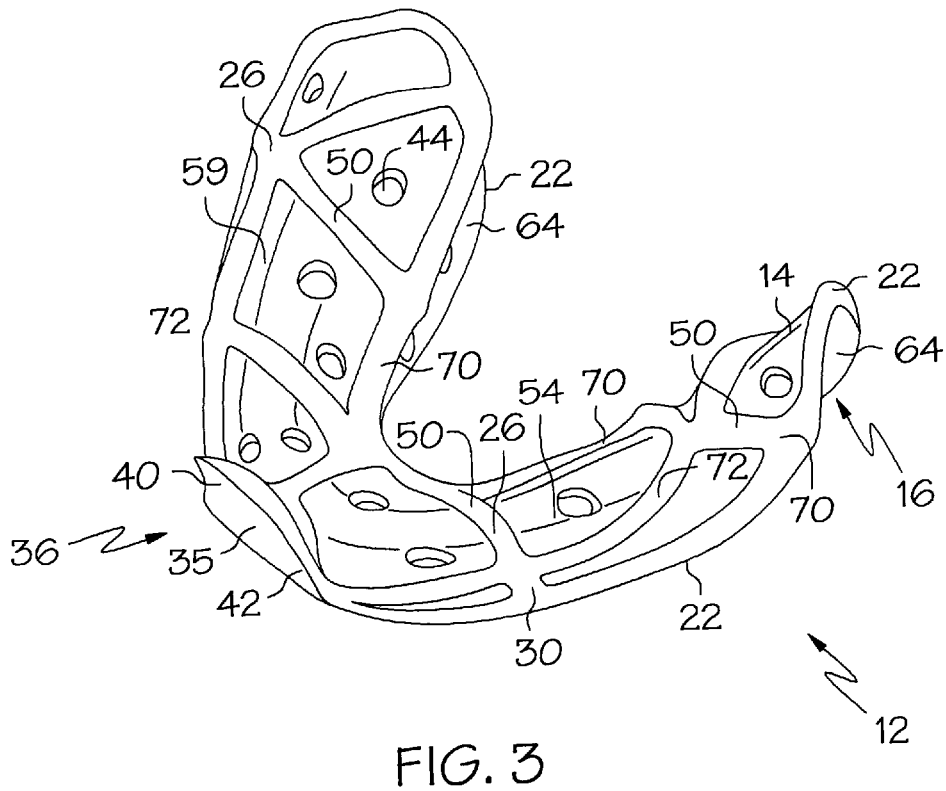
FIG. 3 is a forward looking aft top perspective view illustration of an exemplary embodiment of a mandibular impression tray of the present invention.
Figure 4:
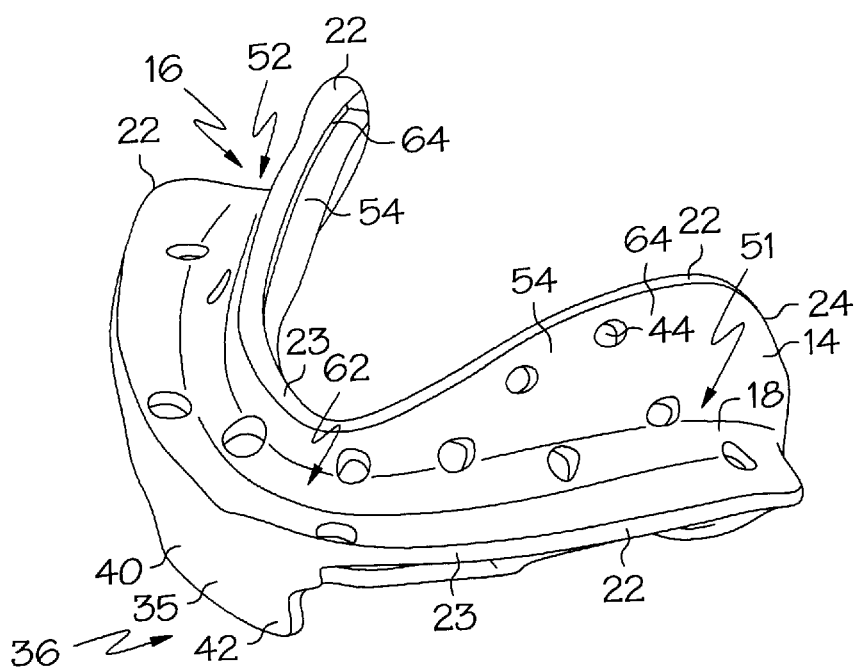
FIG. 4 is a forward looking aft bottom perspective view illustration of the mandibular impression tray illustrated in FIG. 3.
Figure 5:
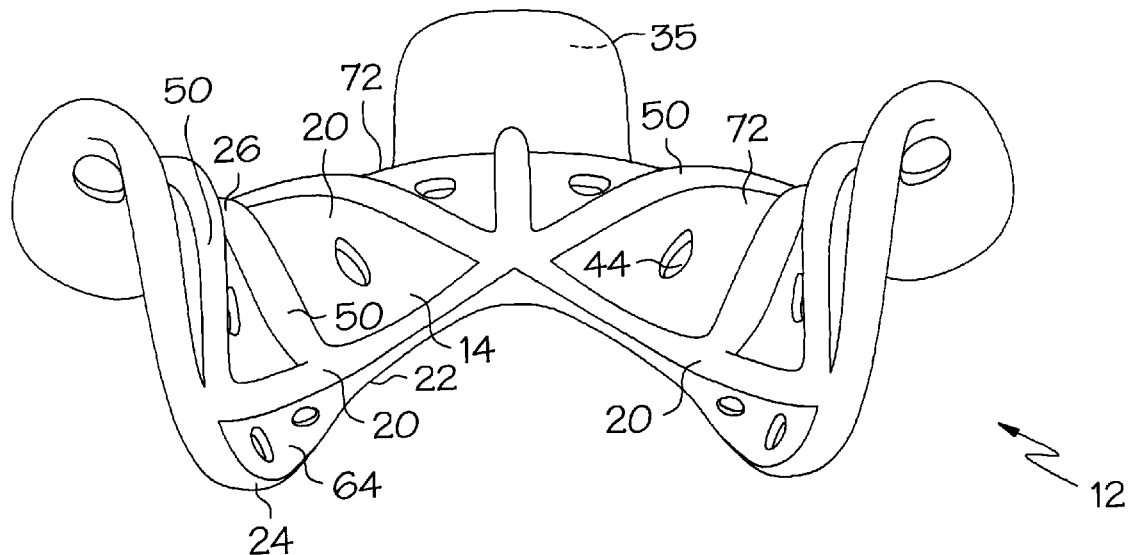
FIG. 5 is an aft looking forward top perspective view illustration of the mandibular impression tray illustrated in FIG. 3.

Illustrated in FIGS. 1 and 2 is an exemplary embodiment of a disposable maxillary impression tray 10 of the present invention and illustrated in FIGS. 3 and 4 is an exemplary embodiment of a disposable mandibular impression tray 12 of the present invention. The disposable dental impression trays are used for making impressions (see 82 and 84 in FIG. 9) of edentulous dental ridges or arches with impressionable material and are made of plastic or some other inexpensive material. The tray material may be made of injection-molded plastic or other plastic or may be a metal. The thinner the tray is, the better the impression in the impression material will be, so long as the tray is sufficiently rigid to prevent and resist deformation of the tray. Thinner trays save plastic material in the tray making process. Thinner trays provides room for centric positioning of the two opposing trays and thus increases the accuracy of the process.

Each of the trays is made of a thin contoured plate 14 having a contour 16 approximating a section of an oral cavity of a mouth of which an impression is to be made. The plate 14 has a impression side 18 for holding impressionable material and an opposite backside 20. A reinforced edge 22 runs around at least a portion 23 of a border 24 of the plate 14 and cross-bracing 26 extends along the backside 20 between a plurality of positions 30 around the reinforced edge. The reinforced edge 22 and the cross-bracing 26 can be formed of thickened lines or beads of the plate material. The thickened line or bead reinforces the plate against deformation under stress.

Figure 6:
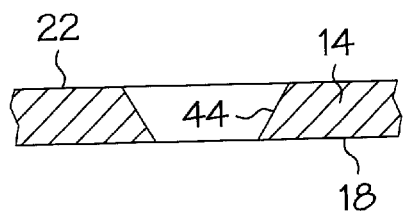
FIG. 6 is a cross-sectional view illustration of an exemplary embodiment of a hole in trays of the present invention.

Each of the exemplary embodiments of the trays illustrated herein has a handle located at a front 36 of the plate 14. The maxillary impression tray 10 has a maxillary handle 34 extending generally normal to and away from the backside 20. The maxillary handle 34 has a flat front surface 40 on a front 42 of the handle. The handle serves to manipulate the tray in the mouth. The mandibular impression tray 12 has a mandibular handle 35 extending generally normal to and away from the backside 20. Holes 44 extend through the plate between the impression side 18 and the backside 20 and are located along the plate 14 between cross-ribs 50 of the cross-bracing 26. The holes 44 are flared outwardly from the impression side 18 to the backside 20, thus the holes are wider at the backside than at the impression side as illustrated in FIG. 6. The holes provide retention of the impression material during the impression making process. The plate 14 has a generally U-shaped trough 51 and the trough has a generally U-shaped cross-section 52. The U-shaped trough 51 has legs 54 extending back and away from the front 36 of the plate 14 and connected by a web 56.

Figure 7:
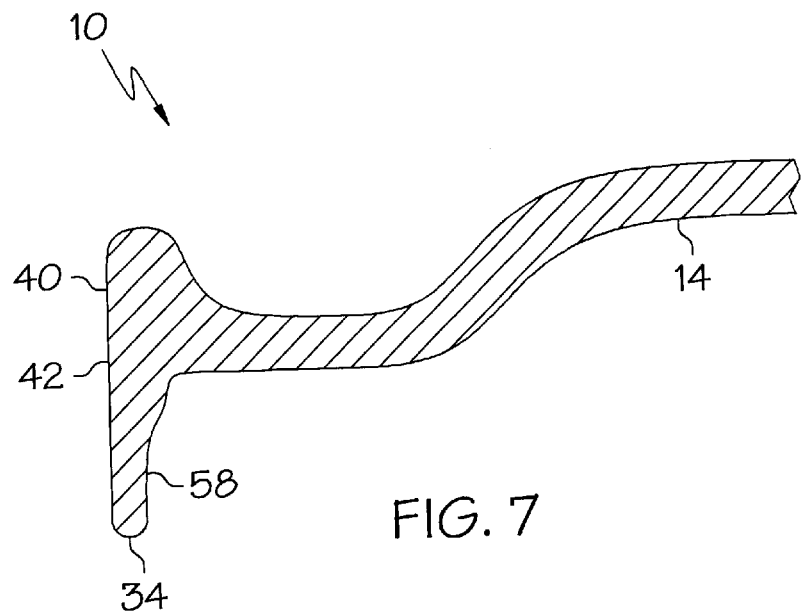
FIG. 7 is a cross-sectional view illustration through 7—7 in FIG. 2.

The disposable maxillary impression tray 10 is illustrated in FIGS. 1 and 2, and has the contour 16 which approximates maxillary gums and a roof of a mouth. The maxillary tray 10 has the flat front surface 40 on the front 42 of the maxillary handle 34 and a back flat surface 58 on a back 60 of the handle as further illustrated in FIG. 7. The flat front surface 40 on the front 42 of the maxillary handle 34 of the maxillary tray 10 may be utilized to record or register the midline of a facial aspect of the patient's appearance as an aid to setting a midline of the arch of prosthetic teeth. The flat front surface 40 may be also be utilized to record the highest extent of the upper lip line, or smile line, of the facial aspect of the patient's appearance.

Illustrated in FIGS. 3 and 4 is the mandibular tray 12 in which the plate 14 is a generally horse-shoe or U-shaped trough 62 with rear arched flanges 64 extending down from a rear of the mandibular tray and the contour 16 approximates mandibular gums of a mouth. The rear arched flanges 64 are designed to displace the tongue when taking an impression of the edentulous mandible and encourages tongue position that permits an impression of the full lingual surface of the edentulous ridge extending from the midline in the anterior portion of the mandible and beyond the muscle attachments in the posterior segments of the mandible.

The cross-bracing 26 of the mandibular tray 12 includes elongated inner and outer lingual bracing members 70 and 72 disposed on the backside 20 of the plate 14 and spaced apart from the edges of the mandibular tray 12. The inner and outer lingual bracing members 70 and 72 provide additional structural rigidity and stability to the mandibular tray 12. The inner and outer lingual bracing members 70 and 72 can be formed of thickened lines or beads of the plate material. The inner lingual bracing member 70 also allows retraction of tissue during the impression making process and helps the patient place the tongue in a position that doesn't interfere with taking the impression of the edentulous mandible.

The back flat surface 58 on a back 60 of the maxillary handle 34 of the maxillary tray 10 may be designed to engage the flat front surface 40 on the front 42 of the mandibular handle 35 of the mandibular tray 12 to provide a guidance plane in positioning centric relation of the opposing dental arches in the patient's mouth. The handle of the trays may be modified or removed after the impression of the mandible and maxilla edentulous dental ridges are obtained when the removal of the handles facilitates the need of the operator.

Figure 8:
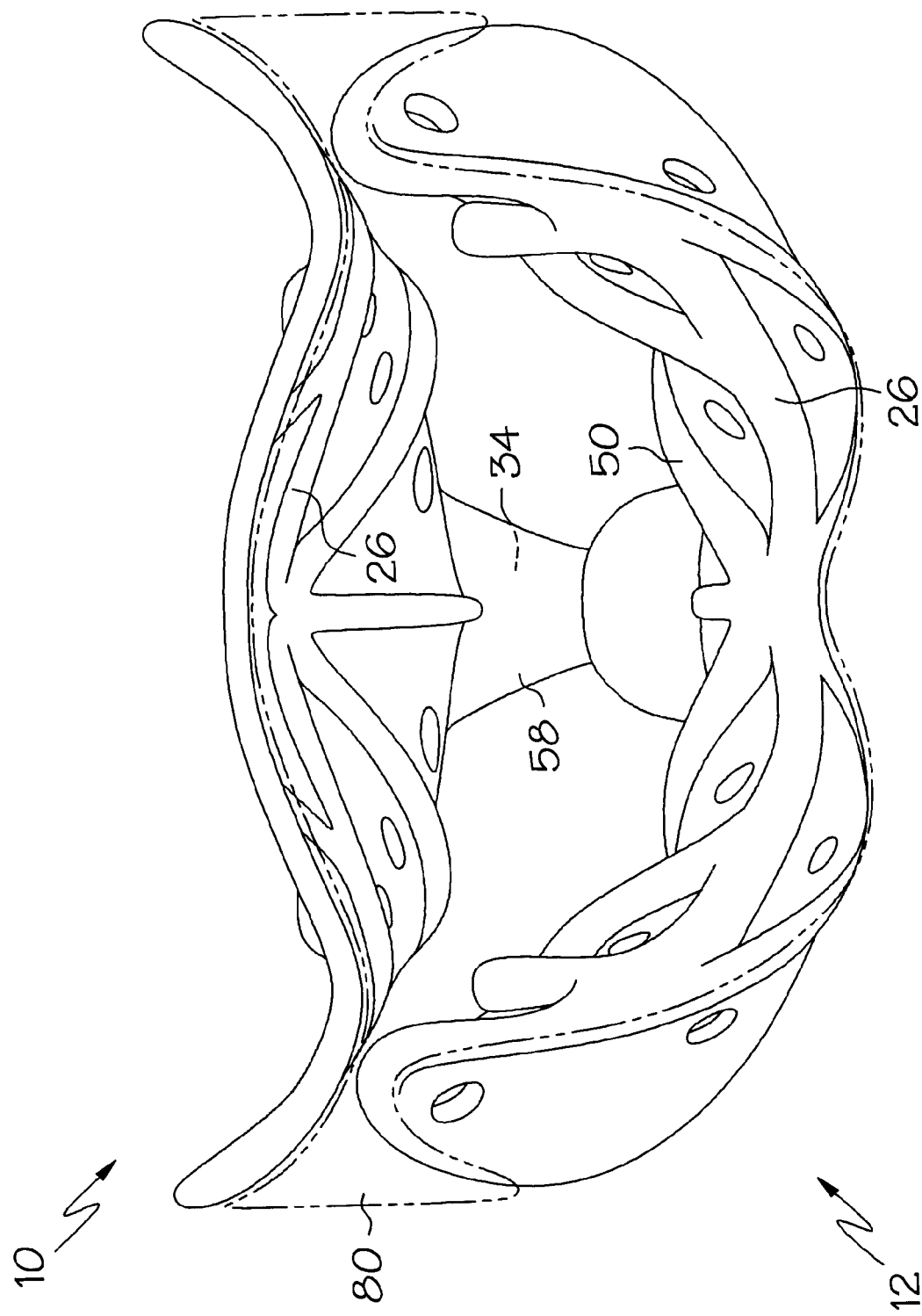
FIG. 8 is an aft looking forward perspective view illustration of the maxillary and mandibular impression trays with bite block formed therebetween.
Figure 9:
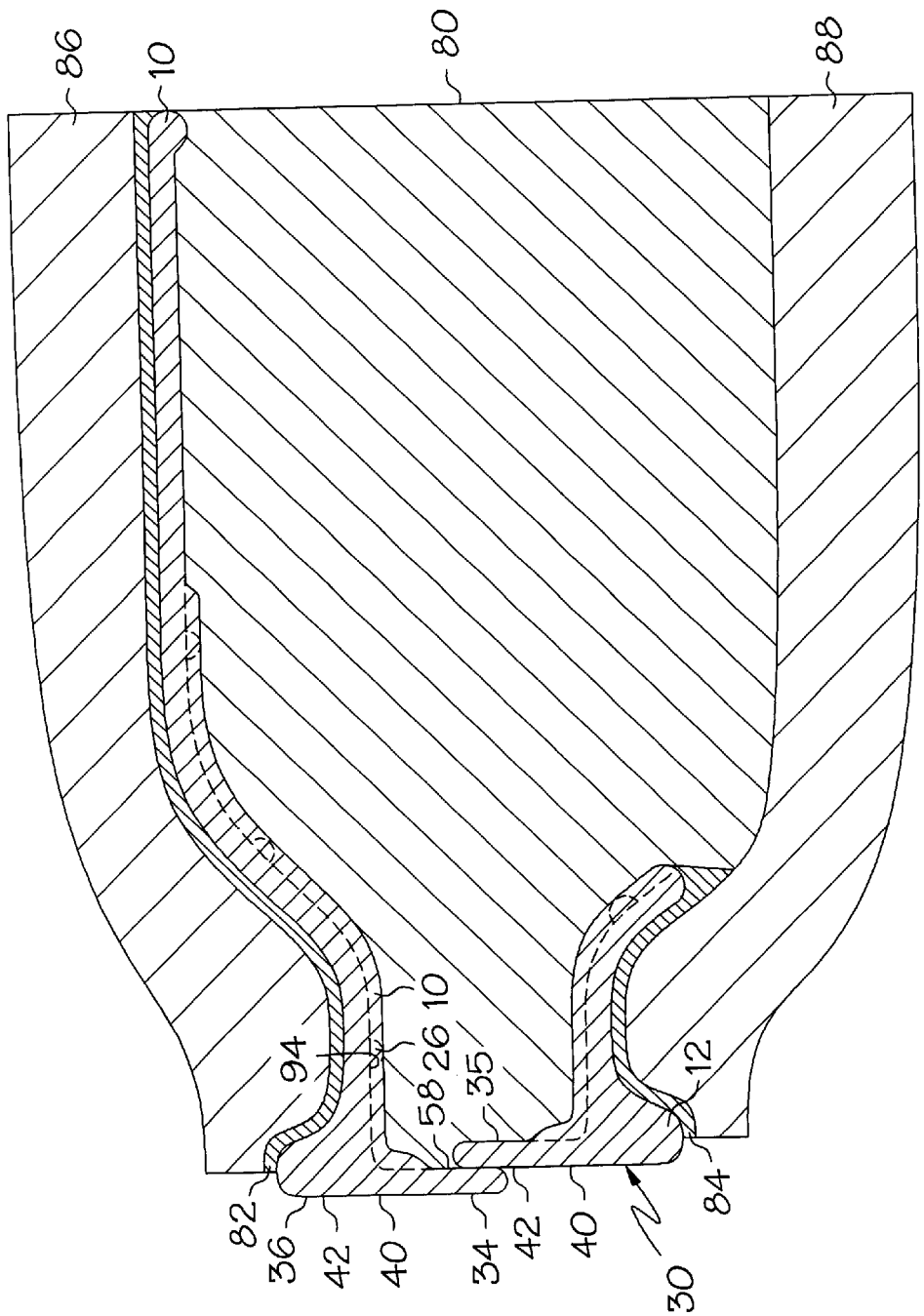
FIG. 9 is a cross-sectional view illustration of the trays and block through 9—9 in FIG. 8.

Illustrated in FIGS. 8 and 9 is a dental impression tray assembly including a bite block 80 between the disposable maxillary and mandibular impression trays 10 and 12. The bite block 80 is formed after the impression material between the edentulous alveolar maxillary and mandibular alveolar ridges 86 and 88, respectively, and the disposable maxillary and mandibular impression trays 10 and 12, respectively, has set to form maxillary and mandibular impressions 82 and 84, respectively. The present invention provides for placing impression material between backsides 20 of the maxillary and mandibular impression trays 10 and 12 while the trays and the maxillary and mandibular impressions 82 and 84 between the ridges and the trays are in the patient's mouth and to form the bite block 80. The bite block 80 facilitates the registration of the bite relationship between the maxilla and the mandible impressions made with the trays of the present invention. The cross-bracing 26 forms registration impressions 94 in the bite block 80 which facilitates registration of the trays and impressions in the trays when placed in an articulator for making plaster molds with which the dentures are manufactured.

The present invention provides a system including the apparatus and methods described above that permits a final impression, the recording of critical information and the registration of the bite relationship necessary for proper denture construction in a single patient appointment.

While the preferred embodiment of the present invention has been described fully in order to explain its principles, it is understood that various modifications or alterations may be made to the preferred embodiment without departing from the scope of the invention as set forth in the appended claims.

Accordingly, what is desired to be secured by Letters Patent of the United States is the invention as defined and differentiated in the following claims:

What is claimed is:

1. A dental impression tray for making impressions of edentulous dental arches with impressionable material, said tray comprising:
    a thin contoured plate of plastic material having a contour approximating a section of an oral cavity of a mouth of which an impression is to be made,
    said plate having a impression side for holding impressionable material and an opposite backside,
    a reinforced edge around at least a portion of a border of said plate, and
    cross-bracing on said backside of said plate wherein at least a portion of said cross-bracing runs at an obtuse angle to said reinforced edge.

2. A tray as claimed in claim 1 further comprising a handle extending generally normal to and away from said backside at a front of said plate.

3. A tray as claimed in claim 2 further comprising holes extending through said plate between said impression side and said backside.

4. A tray as claimed in claim 3 wherein said holes are located along said plate between cross-ribs of said bracing.

5. A tray as claimed in claim 4 wherein said holes are flared outwardly from said impression side to said backside.

6. A tray as claimed in claim 1 wherein said plate includes U-shaped trough and said trough has a U-shaped cross-section.

7. A tray as claimed in claim 6 wherein said U-shaped trough has legs extending back and away from a front of said plate.

8. A tray as claimed in claim 7 further comprising a handle extending generally normal to and away from said backside at said front of said plate.

9. A tray as claimed in claim 8 further comprising a flat surface on a front of said handle.

10. A tray as claimed in claim 1 wherein said tray is a maxillary tray and said contour approximates maxillary gums and a roof of a mouth and said cross-bracing includes a first portion of a plurality of bracing ribs extending away from a plurality of positions around said reinforced edge.

11. A tray as claimed in claim 10 wherein said tray said cross-bracing includes at least one of said bracing ribs extending between at least two others of said bracing ribs.

12. A tray as claimed in claim 10 further comprising a handle extending normal to and away from said backside at a front of said plate.

13. A tray as claimed in claim 12 further comprising holes extending through said plate between said impression side and said backside.

14. A tray as claimed in claim 13 wherein said holes are located along said plate between cross-ribs of said bracing.

15. A tray as claimed in claim 12 further comprising a front flat surface on a front of said handle and a back flat surface on a back of said handle.

16. A tray as claimed in claim 10 wherein said plate includes U-shaped trough and said trough has a U-shaped cross-section.

17. A tray as claimed in claim 1 wherein said tray is a mandibular tray, said plate is a generally U-shaped trough with rear arched flanges extending down from a rear of said tray and, said contour approximates mandibular gums of a mouth.

18. A tray as claimed in claim 17 further comprising:
    transversely spaced apart elongated inner and outer lingual members running in a generally lingual direction on said backside and spaced inwardly of inner and outer U-shaped portions respectively of said reinforced edge,
    said cross-bracing having a plurality of bracing ribs, and
    a portion of said bracing ribs extending across said backside between said inner and outer lingual members.

19. A tray as claimed in claim 18 wherein said tray said cross-bracing includes at least one of said bracing ribs extending from said inner member across said outer member to said outer U-shaped portion.

20. A tray as claimed in claim 18 further comprising a handle extending normal to and away from said backside at a front of said plate.

21. A tray as claimed in claim 20 further comprising holes extending through said plate between said impression side and said backside.

22. A tray as claimed in claim 21 wherein said holes are located along said plate between cross-ribs of said bracing.

23. A tray as claimed in claim 19 wherein said U-shaped trough has a U-shaped cross-section.

* * * * *